(12) United States Patent
Mead et al.

(10) Patent No.: US 7,527,021 B2
(45) Date of Patent: May 5, 2009

(54) NON-INVASIVE DRUG SELF-ADMINISTRATION SYSTEM FOR ANIMALS

(75) Inventors: Andy N. Mead, Widford (GB); David N. Stephens, Brighton (GB); Kevin Lease, Columbia, MO (US); Jay Hirsh, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 609 days.

(21) Appl. No.: 11/189,042

(22) Filed: Jul. 22, 2005

(65) Prior Publication Data
US 2007/0006814 A1 Jan. 11, 2007

Related U.S. Application Data

(63) Continuation-in-part of application No. PCT/US2004/001839, filed on Jan. 23, 2004.

(60) Provisional application No. 60/442,292, filed on Jan. 24, 2003, provisional application No. 60/674,208, filed on Apr. 22, 2005.

(51) Int. Cl.
*A01K 1/03* (2006.01)
*A01K 29/00* (2006.01)

(52) U.S. Cl. .................................................... 119/420
(58) Field of Classification Search ................. 119/420, 119/452, 464, 476, 666; 222/4; 239/8, 9, 239/373; 134/177
See application file for complete search history.

(56) References Cited

U.S. PATENT DOCUMENTS

| 4,567,856 | A | * | 2/1986 | Sorenson | 119/666 |
| 5,056,467 | A | * | 10/1991 | Schaefer | 119/666 |
| 5,513,798 | A | * | 5/1996 | Tavor | 239/8 |
| 6,003,789 | A | * | 12/1999 | Base et al. | 239/433 |
| 6,554,202 | B2 | * | 4/2003 | Ganan-Calvo | 239/8 |
| 2002/0023667 | A1 | * | 2/2002 | Pham | 134/18 |

* cited by examiner

*Primary Examiner*—Rob Swiatek
(74) *Attorney, Agent, or Firm*—Rodney L. Sparks

(57) ABSTRACT

A system for allowing animals to self administer drugs via intranasal absorption. The system comprises an aerosol dispersing apparatus (1) connected to a source of pressurized air (5) for ejecting a pharmaceutical composition contained in a reservoir (8) out of the aerosol dispersing apparatus nozzle head (3) and into a sensing chamber (12) when a sensor (16) detects the presence of an animal in the sensing chamber (12). The system can be used to study the addictiveness of new drugs as well as providing a model system for small animals, such as the mouse, to studying behavioral and physiological responses to addictive drugs.

7 Claims, 7 Drawing Sheets

NON-INVASIVE DRUG SELF-ADMINISTRATION SYSTEM FOR ANIMALS

RELATED APPLICATIONS

This application is a national stage filing and continuation-in-part of International Application No. PCT/U.S.2004/001839, filed on Jan. 23, 2004, which claims priority under 35 USC §119(e) to U.S. Provisional Application Ser. No. 60/442,292, filed Jan. 24, 2003, and this application also claims priority under 35 USC §119(e) to U.S. Provisional Application Ser. No. 60/674,208, filed Apr. 22, 2005, the disclosures of which are hereby incorporated herein by reference in their entirety.

U.S. GOVERNMENT RIGHTS

This invention was made with United States Government support under Grant Nos. GM 27318, awarded by the National Institutes of Health. The United States Government has certain rights in the invention.

BACKGROUND

Addiction to drugs of abuse is a serious affliction of the human population, leading to enormous governmental expenditures and having negative impacts on the lives of many people. The best accepted animal model for drug abuse is self-administration, in which animals are trained to perform an action that leads to drug administration. Animals will self-administer many drugs of abuse, and the degree of self-administration is a measure of abuse liability. The extent to which an animal will work to obtain drug is a measure of its motivation for the drug, and is a measure of drug craving, an important aspect of the addictive process of humans.

A common means of drug self-administration in animal models is via an indwelling catheter implanted into the jugular, or other vein. This method requires difficult surgery, including anesthesia, and involves some degree of suffering to the animal. While commonly used in primates, and feasible in large rodents such as rats, intravenous drug self-administration is difficult in smaller rodents such as the genetically tractable animal model, the mouse. Although techniques have been described for implantation of intravenous catheters in the mouse, and such methods are used in animal experimentation, their utility is limited, since the catheters cannot be extended into the heart without severe tissue damage. Thus the intravenous catheters become blocked within a period of a few days after implantation, limiting the extent to which an individual animal can be studied.

The present invention is directed to a device and method for non-invasive self-administration that works efficiently in the mouse, and should be applicable to a wide variety of animal models. Since this method does not require surgery, it is easier to establish, and does not suffer the disadvantage of catheter blockade, allowing a full behavioral analysis of self-administration behavior not possible with intravenous administration. Additionally, since people ingest some drugs by inhalation, this method provides a more realistic model for this class of drugs.

SUMMARY OF VARIOUS EMBODIMENTS OF THE INVENTION

The present invention is directed to a device for animal self-administration of pharmaceutical compositions as well as a methodology for establishing such self-administration. The method comprises the use of a system for administering a highly focused aerosol drug composition based on a physical act performed by the animal. More particularly, the system comprises a device for administering an aerosolized drug composition whenever an animal comes within a preselected distance of the nozzle of the aerosol device. The presence of the animal within the target region is detected by a sensing device that produces a signal that results in the aerosol device releasing a preselected amount of the drug composition.

BRIEF DESCRIPTION OF THE DRAWINGS

FIG. 2A is a top cross sectional view of the airbrush (20) wherein the pin valve (21) contained within annular sleeve (40) of the airbrush (20) has been attached to a solenoid (24). FIG. 2B is a side cross sectional view of the aerosol dispersing apparatus showing the airbrush (20) mounted on a block (25) wherein the block (25) and the solenoid (24) have been attached to a base (28). FIG. 2C is a side cross sectional view of the front end of the airbrush (20) showing the fluid reservoir (8), the annular sleeve (40) and a reservoir passageway (9) that allows fluid communication between the fluid reservoir (8), the annular sleeve space (42) and an annular sleeve port (43), wherein a pin valve (21) functions to regulate flow of the reservoir fluid from the fluid reservoir to the nozzle (3) of the airbrush (20).

Figure 1:
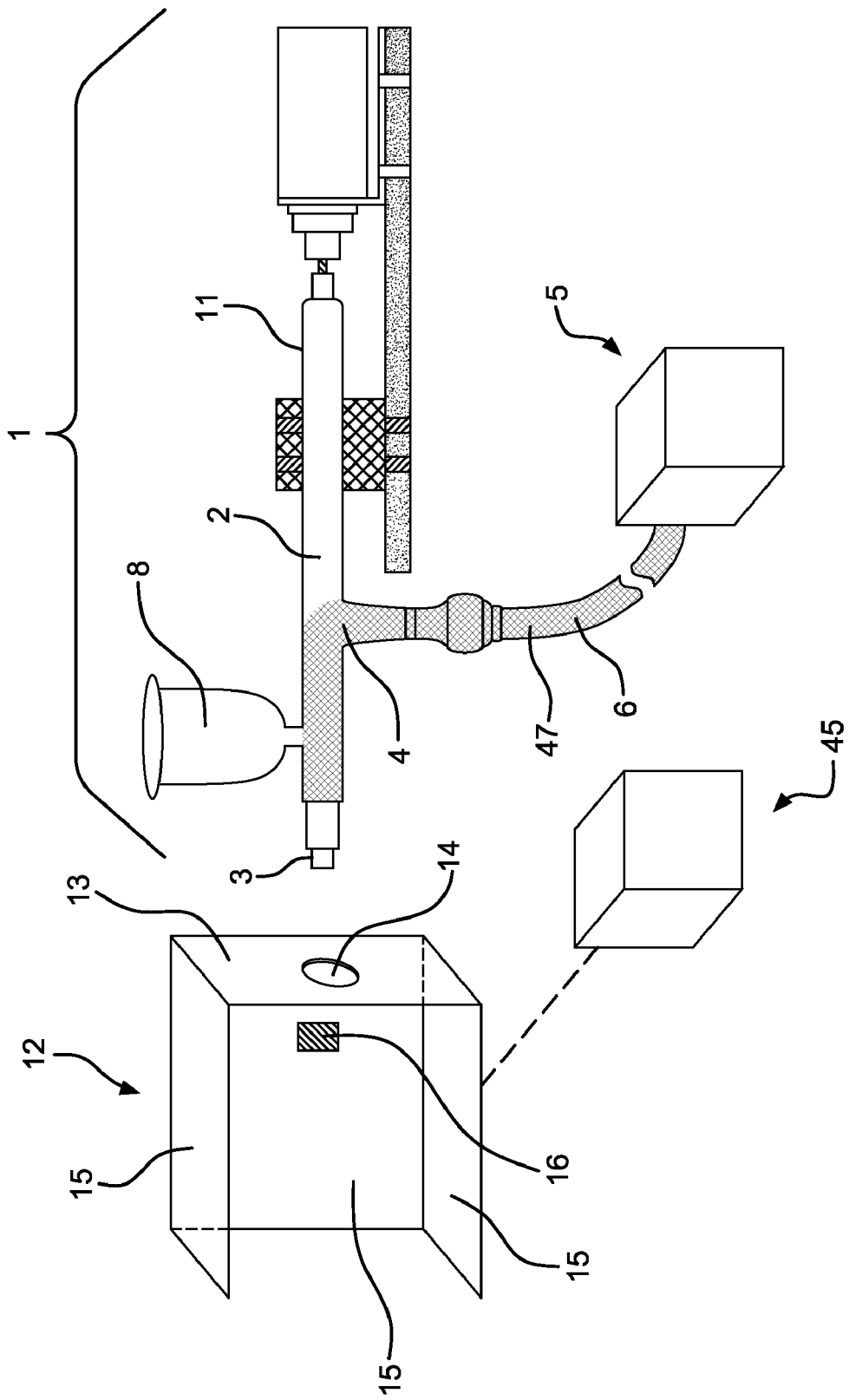
FIG. 1 represents a schematic drawing of the self administering system of the present invention. The system comprises an aerosol dispersing apparatus (1), a sensing chamber (12), an air valve (47), an animal cage (45), and means for communicating a signal produced by a sensor (16) in the sensing chamber (12) to activate the aerosol dispersing apparatus (1) to spray a dose of a composition contained within the fluid reservoir (8) into the sensing chamber (12) in an aerosolized form. Cross hatches in FIG. 1 between the source of pressurized air (5) and the nozzle head (3) indicate the possible locations of the air valve (47) as described further below.

FIFS. 6A-6D are views of an exemplary illustration of the airbrush parts, not to scale.

DETAILED DESCRIPTION OF EMBODIMENT

Definitions

In describing and claiming the invention, the following terminology will be used in accordance with the definitions set forth below.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "sensor" or "detector" includes any device that is capable of detecting the presence or movement of an object within a specified field. Such devices include but are not limited to motion detectors, electric eyes, pressure sensitive switches and video surveillance equipment.

As used herein, the term "bonded" is defined as an air tight seal that fixes two components to one another along the entire contacted surfaces.

Embodiments

Addiction to drugs of abuse is a serious affliction of the human population, leading to enormous governmental expenditures and having negative impacts on the lives of many people. The best accepted animal model for drug abuse is self-administration, in which animals are trained to perform an action that leads to drug administration. There is a need for a model system that works efficiently to allow an animal, particularly small animals, such as mice, hamsters, gerbils and the like, to self administer a pharmaceutical agent. Furthermore the system should be adaptable to a wide variety of animal models. The present invention is based on a system that releases a drug of interest in an aerosol form, based on the animal's own actions, resulting in self-administration of the drug. Since this system does not require surgery, it is easier to establish, and does not suffer the disadvantage of catheter blockade, allowing a full behavioral analysis of self-administration behavior that is not possible with intravenous administration. Additionally, since people ingest some drugs by inhalation, this method provides a more realistic model for this class of drugs.

One aspect of the present invention is directed to a system for self-administration of a pharmaceutical composition. The system comprises a device for administering an aerosolized dose of the desired drug composition to the animal, a sensor for detecting the presence of an animal within a targeted area and generating a signal, and a triggering element that receives the signal and activates the aerosol dispersing apparatus to release a drug dose. Thus the triggering element provides electronic or mechanical communication between the aerosol dispersing apparatus and the sensor such that an interaction between the animal and the sensor causes the aerosol dispersing apparatus to release an aerosolized dose of the drug to the animal. Suitable triggering elements are known to those skilled in the art and will vary based on the model animal used for testing.

In one embodiment the sensor is a pressure sensitive device or lever that emits a signal when the animal contacts or places weight on a target area. In one embodiment a pressure sensitive device is located on or near the walking surface of the cage such that a signal is generated whenever the animal steps on a preselected area. In another embodiment the sensor is an infrared detector or an electronic eye and the animal's disruption of the infrared beam causes the generation of a signal by the sensor. Such sensors can be located in a variety of positions inside the sensing chamber, and in one embodiment the sensor is located on the interior side wall of the sensing chamber. For example, in one embodiment the triggering element comprises a commercially available nose-poke detector (e.g. part of Animal Behavior Environment Test System available from Lafayette Instrument).

The aerosol dispersing apparatus component of the self administering system comprises a fluid reservoir for holding the drug composition and means for producing and releasing a fine suspension of a dose of the drug composition. Aerosol devices have previously been described in U.S. Pat. Nos. 4,079,893, 4,978,072, 5,660,166, 6,263,872 and 6,354,517, the disclosures of which are incorporated herein. Such devices can be modified to allow the device to administer a preselected dose amount after a signal has been generated by the sensor. Electronic means, including hardware and software, for producing and analyzing a signal generated from the sensor and producing an effect based on the signal received from the sensor are commercially available (e.g. Animal Behavior Environment Test System, Lafayette Instrument). For example, software is commercially available that can be programmed to determine the quantity or quality of the signal generated from the sensor required before signaling an actuator to release a dose from the aerosol dispersing apparatus. In one embodiment the software may also regulate the dosage amount that is administered for a given experiment or for each signal generated by the sensor.

In accordance with one embodiment a system for the self administration of pharmaceutical formulations is provided wherein the system comprises a drug dispensing apparatus, means for detecting the presence of an animal within a target location, and means for triggering the dispensing of the drug. Preferably, the drug dispensing apparatus will dispense the pharmaceutical composition in an aerosol form and the detection means will only trigger the dispensing of the pharmaceutical composition when the animal is with in sufficient proximity to the dispenser to inhale an effective/physiologically relevant dose of the pharmaceutical composition.

In one embodiment, shown in FIG. 1, the aerosol dispersing apparatus (1) comprises a barrel (11) having a front and back end, with a barrel wall extending between the front and back end and defining an interior barrel space (2). The front end of the barrel is provided with an aerosolizing nozzle head (3) that allows fluid communication between the interior barrel space (2) and the exterior of the barrel. The dimensions of the barrel are not critical, however the barrel is provided with a barrel port (4) that allows communication between the interior barrel space (2) and a source of pressurized air (5). Typically, the source of pressurized air is connected to the barrel port (4) via an air passageway (6). In one embodiment the air passageway comprises an airtight conduit or flexible tubing. In one embodiment, an air valve, biased in a closed position, is positioned between the nozzle head and the source of pressurized air and this air valve regulates the flow of air from the source of pressurized (5) air through the interior barrel space (2) and out the nozzle head (3). Alternatively, the flow of air can be regulated by turning the power on or off to a source of air flow (e.g. an air compressor). In one embodiment the source of pressurized air (5) is connected to the barrel port (4) through an air passageway (6) and the air valve is located within the air passageway (6) or adjacent to the barrel port (4). In another embodiment the air valve is located adjacent to or within the nozzle head (3). When the air valve is open, air flows from the source of pressurized air (5)

through a connecting air passageway (6) into the interior barrel space (2) and out through nozzle head (3). The aerosol dispersing apparatus is further provided with a drive element for applying force in a manner so as to open the air valve, a release actuator for actuating the drive element and a programmable microprocessor which receives information from a sensor and forwards information to the release actuator to open the air valve and release air into the barrel interior space.

The source of pressurized air may constitute a single use source of compressed air. For example, in one embodiment the source of compressed air comprises a compressed air cartridge that can be removably coupled to the system. Alternatively, the source of compressed air may comprise an air compressor that provides a renewable source of pressurized air to the aerosol dispersing apparatus. Typically the air released from the source of pressurized air is compressed to a pressure of about 1 to about 6 psi, and in on embodiment the air is compressed to a pressure of about 2 to about 4 psi, and in another embodiment the air is compressed to approximately 2 psi.

The aerosol dispersing apparatus is further provided with a fluid reservoir (8) said fluid reservoir having a hollow body for retaining said fluid disposed therein, and a fluid passageway (9) communicating between the fluid reservoir (8) and the barrel interior space (2). In one embodiment the fluid reservoir (8) is fixed to the exterior of the aerosol dispersing apparatus (1). The fluid contained in the fluid reservoir (8) is retained until the air valve is opened allowing air to flow through the interior barrel space (2) creating a venturi effect that assists in drawing fluid out of the fluid reservoir (8) and out through the nozzle head (3) in an aerosolized form. In another embodiment the device is further provided with a reservoir valve, contained within the shaded area of interior barrel space (2) of FIG. 1, wherein the reservoir valve is biased in a closed position, and functions to regulate fluid flow from the fluid reservoir (8) to the barrel interior space (2). In the embodiment that includes a reservoir valve, the aerosol dispersing apparatus is further provided with a drive element for applying force in a manner so as to open the reservoir valve, a release actuator for actuating the drive element and a programmable microprocessor which receives information from a sensor and forwards information to the release actuator to open the reservoir valve and release the fluid formulation into the interior barrel space.

The programmable microprocessor used in the present invention can be programmed to receive information from a sensor wherein the microprocessor then forwards a signal to a release actuator that opens the air valve or opens the air valve and the reservoir valve. In addition, in one embodiment the microprocessor will allow for the regulation of the length of time that the fluid formulation flows into the interior space as well as the length of time the air valve is open (and thus the length of time the aerosolized formulation is released). Typically the aerosol formulation will be released as a brief spray over a period of time from between 50 and 1,000 msec, and in one embodiment the aerosol formulation is released over a period of time ranging from about 100 to 500 msec and in one embodiment the aerosol formulation is released over a period of time of about 250 msec.

The volume of the fluid formulation released into the barrel interior space will vary based on the pharmaceutical to be administered and the subject animal receiving the dose, but typically volumes will be kept under 10 ul. In one embodiment the volume of the fluid formulation released into the barrel interior space will be less than 5 ul and in one embodiment the volume to be released will range between about 2 to about 4 ul and in one embodiment the volume will be about 2.5 ul.

The signal for activating the aerosol dispersing apparatus (1) is generated in response to the presence of an animal in sufficient proximity of the nozzle head (3) of the aerosol dispersing apparatus (1) to receive an intranasal effective dose of the dispensed pharmaceutical. The presence of the animal positioned in an appropriate location to receive an administered dosage intranasally is detected using standard electronic surveillance and detection devices, including electronic eyes, pressure sensitive detectors and motion detectors. In one embodiment a sensor (16) is positioned so as to detect the presence of an animal, and emit a signal, when an animal is located within about 2 to about 0.05 cm of the aerosol dispersing apparatus nozzle head (3), and in one embodiment the sensor emits a signal when the animal is located about 1 to about 0.1 cm, and in another embodiment about 0.5 cm, from the aerosol dispersing apparatus nozzle head (3). In one embodiment the nozzle head (3) and sensor (16) are housed in a unit (i.e. a sensing chamber, 12) that is attachable to standard cages used for the subject animal. In one embodiment, (see FIG. 1) the sensing chamber (12) comprises an end plate (13) provided with a end plate port (14) and a plurality of walls (15) extending away from the end plate (13) and forming an open end chamber. The end plate port (14) is formed for receiving the nozzle head (3) of the aerosol dispersing apparatus (1), and the nozzle head (3) is positioned within or near the end plate port (14) so as to allow dispersion of the aerosolized formulation into the sensing chamber. The sensor (16) will be positioned within, or be formed as an integral part of, the sensing chamber (12) in a manner that allows the sensor to detect the presence of an animal in position to receive the pharmaceutical.

In accordance with one embodiment the sensing chamber will have dimensions that allow at least the nose of the animal to fit within the chamber and come within sufficient proximity to the nozzle head to trigger the sensor. In one embodiment the chamber has a size and dimension that allows the entire animal to enter the chamber. The chamber can be in any desired shape including cylindrical, square or multi-sided. In addition, the chamber may be conical in shape, having an entrance with a greater circumference than the cross sectional circumference of the chamber end plate. In one embodiment the sensing chamber comprises a plurality of side walls and an end plate, wherein the side walls each have an anterior edge, a posterior edge and two lateral edges. In this embodiment the lateral edges of each side wall are bonded to the lateral edges of an adjacent side wall to define an interior space, and the posterior edges are each bonded to the same planar surface of the end plate, wherein the anterior edge of the side walls defines an anterior opening into the interior space. In one embodiment the anterior edge of the side walls are provided with extensions for attaching the sensing chamber to a standard animal cage. In accordance with one embodiment the sensing chamber comprises a square shaped end plate and four equally sized rectangular side walls that are bonded to one another at right angles and bonded perpendicularly to the end plate.

In accordance with one aspect of the present invention a system for the self administration of pharmaceutical formulations comprises a sensing chamber, an aerosol dispersing apparatus and electronic communication means for transmitting a signal from a sensor to an actuating circuit that detects the signal and actuates the aerosol dispersing apparatus to administer the pharmaceutical composition. In one embodiment the sensing chamber comprises a plurality of side walls and an end plate, wherein the side walls project away from the end plate and define a chamber interior space. The sensing device is further provided with a port formed in the end plate and having sufficient dimensions to allow the nozzle from a drug dispenser to spray an aerosolized formation into the chamber interior space. The sensing chamber is further provided with a sensor that produces a signal when an object is present in the interior space of the sensing chamber and within a preselected distance of the aerosol dispersing apparatus nozzle.

The aerosol dispersing apparatus of one embodiment of the present system comprises a barrel having a front and back end wall, and a barrel wall that defines an interior barrel space, wherein an aerosolizing nozzle head is fastened to the front end of said barrel and is in communication with the barrel interior chamber and the exterior of the barrel. The interior space of the barrel is in communication with a source of pressurized air, wherein communication between the pressurized air source and the interior barrel space is regulated by an air valve. The barrel (11) is further provided with a fluid reservoir (8) an annular sleeve (40) located within the interior barrel space (2) and extending parallel to the barrel wall (7) and a fluid passageway (9) that allows fluid communication between the fluid reservoir (8) the interior of the annular sleeve (40). The walls of the annular sleeve define an annular sleeve space (42) and an annular sleeve port (43) wherein the annular sleeve port (43) is in fluid communication with fluid reservoir (8). The annular sleeve (40) is further provided with a pin valve (21) that functions as the reservoir valve to regulate flow of fluid from the fluid reservoir (8) out the nozzle head (3). The pin valve (21) is positioned within the annular sleeve space (42) and extends parallel to the annular sleeve walls through a back wall port formed in the back end wall of the barrel (11). The anterior portion of said pin valve (21) is formed to seal the annular sleeve port (43), by physically blocking the port when the pin valve is in its resting state, thus blocking fluid flow from the fluid reservoir (8) and annular sleeve space (42) and out the nozzle head (3). The posterior end of the pin valve (21) protrudes through the barrel end wall and is attached to biasing means for moving the pin valve axially away from the front end of said barrel, wherein said axial movement breaks the seal between the pin valve (21) and the annular sleeve port (43) and allows the flow of fluid from the annular sleeve space (42) out through the nozzle head (3). Air moving through the interior barrel space (2) creates a venturi effect that assists in drawing fluid out of the annular sleeve space (42) out through the nozzle head (3). In one embodiment the posterior end of the pin valve is attached to a solenoid (24), wherein activation of the solenoid (24) pulls the pin valve (21) in an axial direction away from the annular sleeve port (43), allowing fluid to move from the fluid reservoir (8) and annular sleeve space (42) to the interior barrel space (2) and out the nozzle head (3) for as long as the solenoid (24) is activated. The pin valve (21) is further-provided with biasing means (e.g. a spring) that moves the pin valve (21) back into its resting position, abutting the rim of the annular sleeve port (43) and preventing fluid flow from the annular sleeve space (42) to the interior barrel space, when the solenoid (24) is deactivated. In one embodiment the pin valve is further provided with biasing means (e.g. a counter spring) that slow the return of the pin valve (21) to its resting position.

In accordance with one embodiment the system for the self administration of pharmaceutical formulations is provided with electronic communication means for transmitting a signal from the sensor to an actuating circuit that detects the signal and actuates the aerosol dispersing apparatus by opening the air valve, or in systems that contain a separate reservoir valve, by opening both the air valve and the reservoir valve. Release of fluid from the fluid reservoir into the barrel interior space in conjunction with release of pressurized air into the barrel interior space ejects the fluid, through the barrel nozzle and into the sensing chamber, in an aerosolized form. In devices comprising an air valve and a reservoir valve, in one embodiment the air valve and the reservoir valve are opened simultaneously, however in other embodiments the air valve is first opened and then the reservoir valve or vice versa. In one embodiment the valves of the apparatus are biased in a closed position and the system is provided with a programmable microprocessor that receives information from a sensor and forwards the information to one or more release actuators. The actuators activates one or more drive elements for applying force in a manner so as to open the air and reservoir valves and dispense a dose of the pharmaceutical composition into the interior barrel space. In one embodiment the valves are opened by the activity of a solenoid. Commercially available programming equipment can be used to vary the response requirement to obtain the pharmaceutical composition, e.g. by requiring that the animal activate the sensor several times before the airbrush is activated.

Figure 2A:
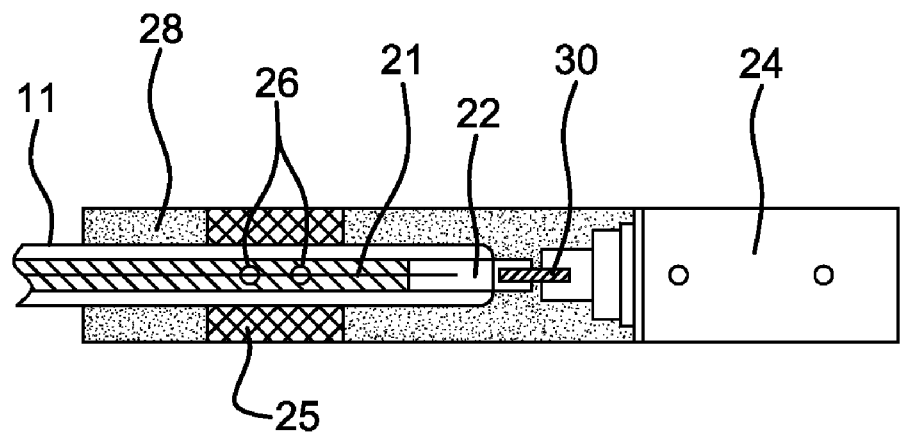
FIGS. 2A-2C represent schematic drawings of an aerosol dispersing apparatus built upon an Iwata Elipse airbrush, wherein the internal valve normally within the coupling is removed such that airflow is controlled only by an external solenoid attached to a pin valve.
Figure 2B:
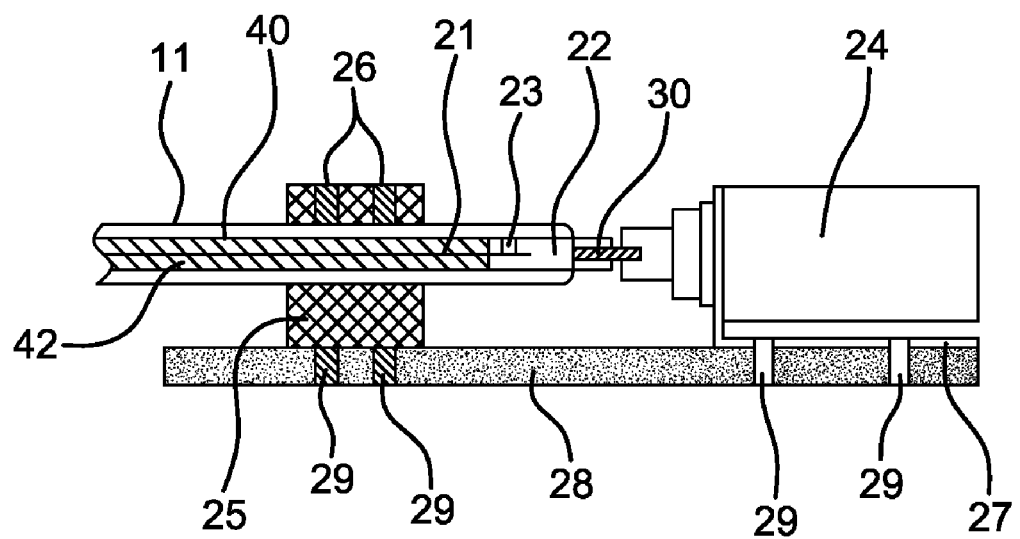
Figure 2C:
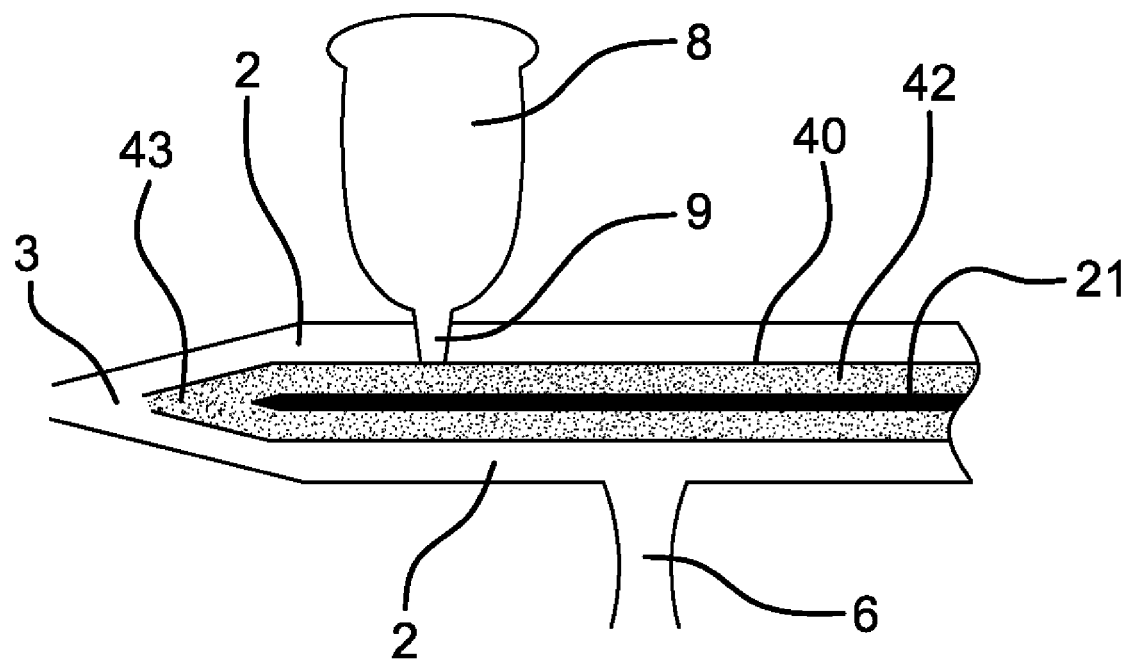
Figure 3:
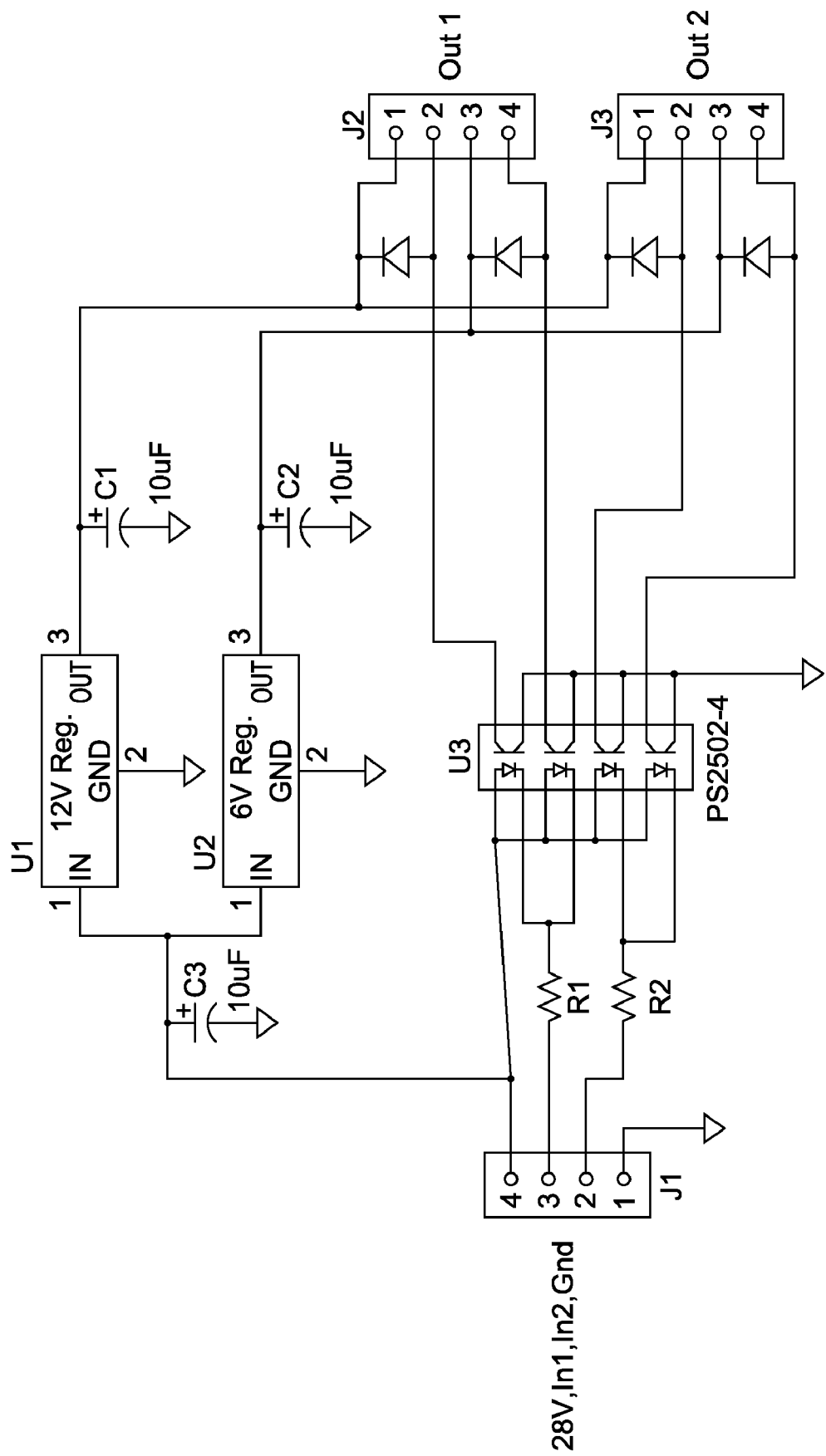
FIG. 3 is a schematic representation of the circuitry used in a release actuator for receiving a signal from the sensor and activating solenoids that open the air and reservoir valves. All diodes are 1N4148, all capacitors are 10 uF radial electrolytic, U1 is a 6V DC regulator, U2 is a 12V DC regulator and U3 is a Photo-Darlington opto-isolator.

In accordance with one embodiment the aerosol dispersing apparatus of the self-administration system comprises a modified graphics arts airbrush that is in electrical communication with a commercial nose-poke detector. In accordance with one embodiment activation of the modified graphics arts airbrush is controlled by an electrical solenoid: (see FIGS. 1 and 2). More particularly, an Iwata Eclipse gravity feed airbrush was modified to form the aerosol dispersing apparatus of the present invention. The Iwata Eclipse airbrush is provided with a fixed reservoir cup (8) and is available with a 0.35 mm or 0.5 mm nozzle & pin valve that allows a liquid drug in the reservoir cup to be sprayed as an aerosol. One modification involved removing the internal valve normally within the coupling such that airflow is controlled by a separate air valve and the fluid flow is controlled by the pin valve that is modified to be connected to an external solenoid (See FIGS. 2A-2C). Accordingly, the air brush was modified by drilling a hole in the back end of the airbrush (opposite to the end provided with the nozzle) and fixing the posterior end of the pin valve (21) onto a rod (22), wherein the rod (22) extends out through the hole formed at the back end of the airbrush. In one embodiment the hole drilled in the back end of the airbrush has the same diameter as the diameter of the rod (22). In one embodiment the rod (22) is clamped onto the pin valve (21) through the use of a setscrew (23), however other means for fixing the pin valve to the rod (e.g. gluing, clamping soldering and the like) can be used in accordance with this invention. The rod (22) is then attached to a solenoid (24) with a threaded stock (30) in a manner such that activation of the solenoid (24) pulls the attached pin valve (21) in an axial direction towards the solenoid (24). In one embodiment the solenoid (24) pulls the pin valve (21) and rod (22) at least 0.1 inches in a direction parallel to the major axis of the airbrush to disengage the pin valve (21) from contact with the rim of the annular sleeve port (43), thus opening the annular sleeve port (43) and the allowing fluid to flow from the annular sleeve space (42) through the annular sleeve port (43). The airbrush barrel (11) and solenoid (24) are typically mounted on a block (25) using mounting set screws (26) to keep the modified airbrush barrel (11) in an elevated position and properly aligned with the solenoid (24). The solenoid is attached to a metal bracket (27) that along with the block (25) is fixed to a base (28) through the use of binding screws (29).

In one embodiment the modified Iwata Eclipse airbrush is attached to a mounting block (25) and the airbrush pin valve

(21) is attached to a bicron solenoid, #STN 3264-002 via a threaded coupling screw (30). The bicron solenoid is controlled via an external 12V power supply. Air is supplied to the airbrush via a standard hose coupling and an external pressure source that is controlled via an air valve actuated by a solenoid. Both the air valve and airbrush pin valve are electronically coupled to a sensing chamber (i.e. a commercially available nose poke detector).

The aerosol dispersing apparatus is mounted into an animal behavior box, which can be modified from a standard model, or purpose built. The nozzle of the airbrush is situated in a recess in one wall of the box, and the entrance to the recess is fitted with a commercial nose-poke detector. When the animal pokes its nose into this detector, it breaks an infrared beam, sending a signal to the computer, which can be programmed to activate the airbrush.

The system can be further provided with a video camera monitoring system to observe the animal's behavior. The video equipment can run continuously, or in one embodiment the video camera is activated only after the animal triggers the sensor. The length of time the camera runs after the animal triggers the sensor can be modified to run for a predetermined time length, or run continuously after the animal triggers the sensor, to observe the animal's behavior during and after receiving the pharmaceutical composition.

The present invention is also directed to the use of the system in a methodology for establishing self-administration. In accordance with one embodiment, animals are first trained to poke their noses into the nose-poke detector for a food reward. They are subsequently trained to obtain a food reward when the airbrush is turned on in response to nose-poke, resulting in a spray of water from the airbrush (to adapt the animal to the spray). Finally, the food reward is allowed to extinguish over a course of days by decoupling the food reward from the nose-poke. In accordance with one embodiment a method for training animals to self administer a composition via inhalation/intranasal absorption is provided. The method utilizes the self administration system of the present invention, wherein the system has been attached to an animal cage to allow a caged animal access to the sensing chamber. The animal cage further comprises a device for administering a food reward and electronic means for distributing the food reward to a region accessible to the caged animal upon triggering the sensor. The method of training the animal comprises the steps of providing a food reward and a dose of aerosolized water upon triggering of the detector by the animal, replacing the water in the reservoir with a pharmaceutical composition; and providing only a dose of the pharmaceutical composition upon triggering of the detector by the animal. In accordance with one embodiment the method further provides a step of providing a food reward and a dose of the pharmaceutical composition upon triggering of the detector by the animal, after the step of replacing the water in the reservoir with a pharmaceutical composition. In accordance with another embodiment the method further provides an initial step of providing a food reward in the absence of a dose of aerosolized water upon triggering of the detector by the animal.

In accordance with one embodiment the animal cage can be fitted with two or more self administration systems, wherein the aerosol dispersing apparatuses administer different pharmaceutical compositions to the mice. In this manner studies relating to relative drug preference or other interactions between two pharmaceutical compositions can be observed. In one embodiment the second aerosol dispersing apparatus can administer pharmacological agents postulated to interfere with the initial drug reward administered by the first aerosol dispersing apparatus. In an alternative embodiment the second aerosol dispersing device can administer water while the first aerosol dispersing device administers a pharmacological preparation. Measuring relative number of nose pokes on each dispensing devise will give relative preference for the pharmacologic agent.

Figure 4:
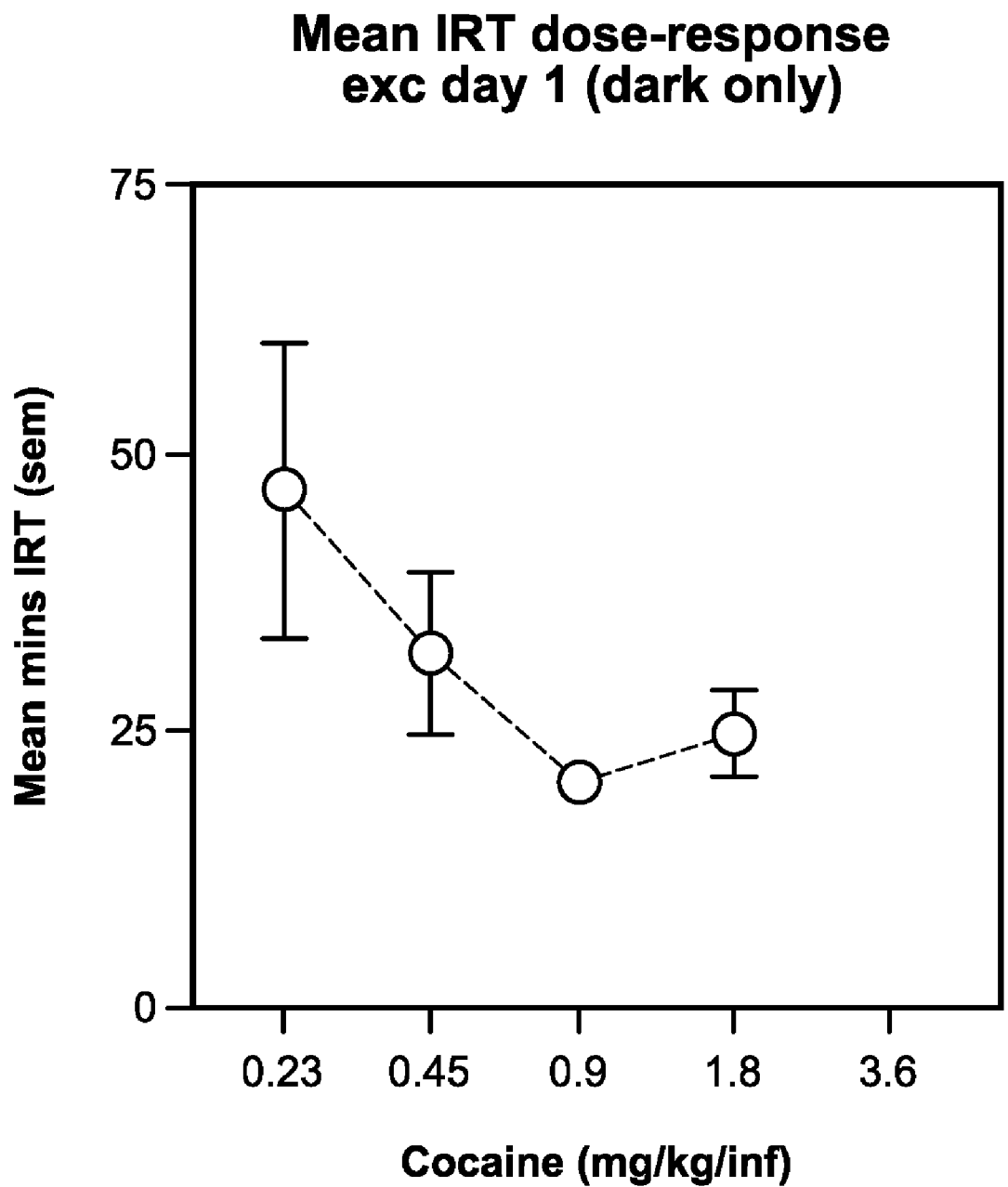
FIG. 4 is a graph representing data (establishing a dose response curve) obtained from mice allowed to self administer a cocaine solution using the system of the present invention. X axis: cocaine HCl dose (mg/kg/infusion). Y axis: mean interval between nose-pokes (minutes).

In one embodiment of the invention animals are tested for self-administration to cocaine by adding cocaine-HCl to the water spray at varying concentrations. At each concentration, for four hours during the animal's daytime, or for another convenient period, an animal is allowed access to the aerosol dispersing apparatus and nose-poke frequencies are recorded. The animals are initially trained to activate the aerosol dispersing device by the following procedure. Animals are first food deprived for 16 h daily, and trained in an operant chamber to poke their noses into the nose-poke detector for a food reward delivered elsewhere in the chamber. They are subsequently trained to perform a nose poke for a food reward despite the nose poke activating the airbrush, resulting in a spray of water from the brush. Finally, the food reward is allowed to extinguish over a course of weeks by decoupling the food reward from the nose-poke. Using this embodiment, as shown in FIG. 4, animals nose-poke to receive the intranasal cocaine most frequently at a cocaine concentration of ~0.9 mg/kg/infusion. At both higher and lower cocaine concentrations there is less self-administration. Such inverted-U shaped dose response curves are also typical for self-administration studies using conventional methods.

Commercially available programming equipment can be used to vary the response requirement to obtain cocaine, e.g. by requiring that the animal perform several nose-pokes before the airbrush is activated. Once responding has been established for one dose of cocaine, other doses may be substituted, or other pharmacological agents postulated to interfere with drug reward administered, or the behavioral contingencies varied. Such lengthy experiments are not routinely possible using intravenous self-administration methods.

EXAMPLE 1

Measuring Cocaine Levels in the Brains of Self Administering Animals

Animals were allowed access to the self administration system of the present invention and the number of nosepokes was recorded using two different concentrations of cocaine (1.8 or 21 mg/kg/spray). Animals were sacrificed within 20 min (animals 3,4) or 1 hr (animals 1,2) of last nosepoke, and all nosepokes occurred within less than 1 hr. Cocaine levels were determined using a commercially available ELISA assay kit (Immunalysis, Inc.) and the results are indicated in Table 1.

Miller et al (1996) show that injection of a pharmacologically active dose of 20/mg/kg cocaine via IP injection (IP=intraperitoneal) yields 0.96 mg/kg cocaine in the brain, so the results present in Table 1 demonstrate that pharmacologically active doses are being achieved with a small number of nosepokes at 21 mg/kg/spray (animals 3,4).

TABLE 1

| Animal | #Pokes × conc | Cocaine conc in brain |
| --- | --- | --- |
| 1 | 6 × 1.8 (mg/kg/spray) | 0.08 (mg/kg) |
| 2 | 4 × 1.8 | 0.28 |
| 3 | 1 × 21.0 | 1.03 |
| 4 | 2 × 21.0 | 2.96 |

EXAMPLE 2

Figure 5A:
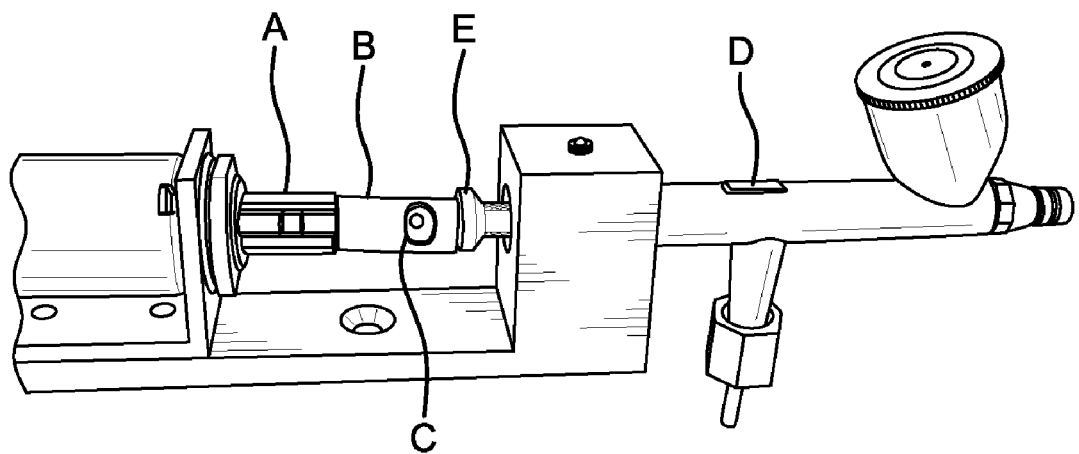
FIGS. 5A, 5B are two views of an exemplary embodiment of the airbrush sprayer.
Figure 5B:
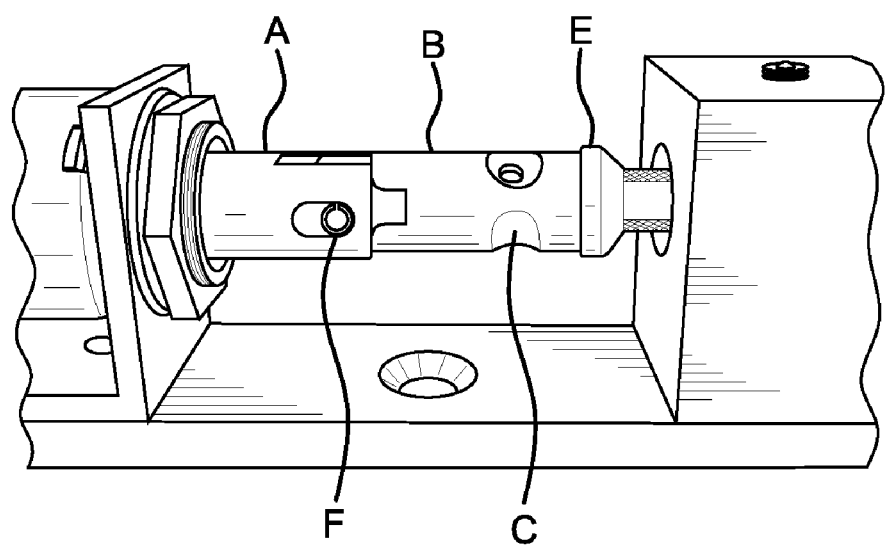
Figure 6A:
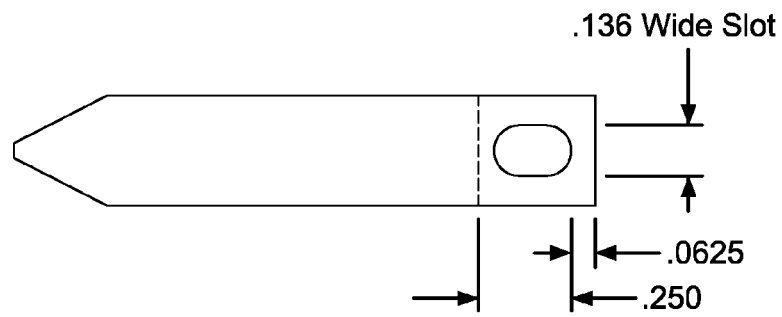
Figure 6B:
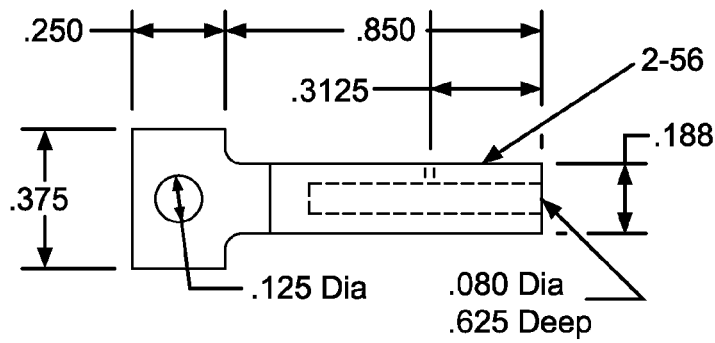
Figure 6C:
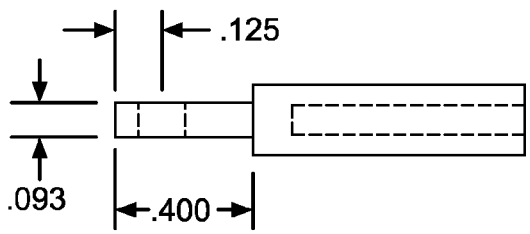
Figure 6D:
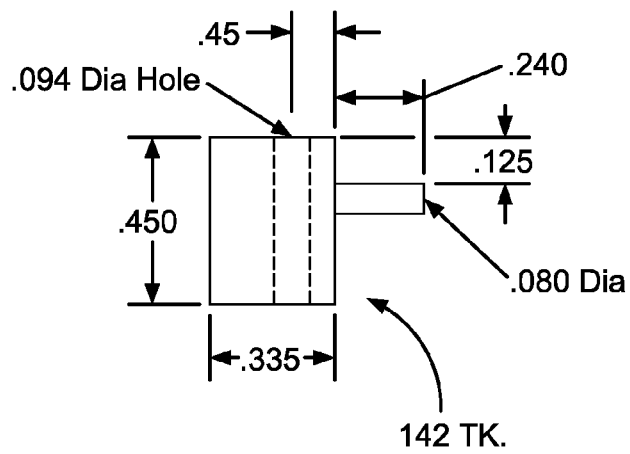

Turning to FIGS. 5 and 6, in an embodiment(s) the finger control is implemented with delrin spacer (D). The delrin spacer serves to provide a forward thrust point for the needle spring, and secondly, the protrusion blocks a hole in the airline such that air is forced forward toward the needle venturi. A slip-coupler is implemented rather than a coupler between solenoid plunger (A) and airbrush needle. The slip-coupler transfers energy of the forward moving solenoid to the airbrush casing via the tygon tubing (B). In an embodiment(s), the plunger (A) is modified to contain an oblong slot; this engages with the brass coupler via a ⅛" roll pin (F). The plunger can move forward relative to the brass coupler (C) which is firmly coupled to the airbrush control needle. When moving forward on disengagement, it slides past the coupler (C) and transfers its forward inertia to the tygon tubing (B). The tygon tubing is cut to a length that engages the solenoid plunger; it contains a hole to allow tightening of the coupler setscrew that tightens on the airbrush needle.

Parts in FIGS. 5 and 6

A: solenoid plunger with machined oblong slot.

B: Tygon tubing

C: Brass coupler

D: Delrin spacer

E: Rear piece of airbrush, cut to length of 1-⅜

F: Roll pin, fits tightly in brass coupler but slides in solenoid plunger.

It should be appreciated that others sizes, dimensions and materials may be utilized without departing from the various embodiments of the present invention.

The invention claimed is:

1. A system allowing for animal self administration of pharmaceutical formulations, said system comprising an animal cage, a sensing chamber, wherein the chamber comprises a plurality of side walls and an end plate, said side walls each provided with an anterior edge, a posterior edge and two lateral edges, wherein the lateral edges of each side wall are bonded to the lateral edges of an adjacent side wall to define a chamber interior space, the posterior edges are each bonded to the same planar surface of said end plate, and the anterior edge of the side walls defines an anterior opening to said chamber interior space; said sensing chamber further provided with a sensor that produces a signal when an object is present in the chamber interior space of the sensing chamber; an aerosol dispersing apparatus comprising a barrel provided with a front and back end wall and a barrel wall that defines an interior barrel space; a nozzle head fastened to the front end wall of said barrel and in communication with the interior barrel space and the exterior of the barrel; a source of pressurized air that is in communication with said nozzle head, wherein communication between the pressurized air source and the nozzle head is regulated by an air valve; a fluid reservoir that is in fluid communication with said interior barrel space, wherein fluid communication between the fluid reservoir and the interior barrel space is regulated by a reservoir valve; a port formed in said end plate and provided with sufficient dimensions to allow unimpeded fluid flow from the nozzle head into the chamber interior space of said sensing chamber; and electronic communication means for transmitting a signal from the sensor to an actuating circuit that detects the signal and actuates driver elements that open the air valve and the reservoir valve.

2. The system of claim 1 wherein the air valve and the reservoir valve are each biased in a closed position and are opened by activation of a solenoid.

3. The system of claim 2 wherein the reservoir valve comprises a pin valve, said pin valve being positioned within an annular sleeve, said annular sleeve located within the barrel interior space and extending parallel to the barrel wall, wherein the walls of the annular sleeve define an annular sleeve space and an annular sleeve port, said annular sleeve port being in fluid communication with fluid reservoir, said pin valve being releasably engaged with said annular sleeve port to regulate flow of fluid from the fluid reservoir out the nozzle head.

4. The system of claim 3 wherein a solenoid is used to disengage the pin valve with the annular sleeve port.

5. A system for training animals to self administer a composition comprising the system of claim 1, wherein said sensing device is attached to the animal cage in a manner that allows an animal present in the cage access to the chamber interior space of said sensing chamber; a food reward dispensing device; and electronic communication means for transmitting a signal from the sensor to an actuating circuit that detects the signal and actuates the food reward dispensing device to release a food reward to a region that is accessible to the caged animal.

6. A method for training animals to self administer a composition intranasally, said method comprising the steps of providing the system of claim 5; introducing the animal to be trained into the animal cage; placing water in said fluid reservoir; providing a food reward and a dose of aerosolized water upon triggering of the sensor by the animal; replacing the water in the fluid reservoir with a pharmaceutical composition; and providing only the pharmaceutical composition dose upon triggering of the detector by the animal.

7. The method of claim 6 further comprising the step of providing a food reward and a dose of the pharmaceutical composition upon triggering of the sensor by the animal, before the step of providing only the pharmaceutical composition upon triggering of the detector.

* * * * *